United States Patent [19]
Clark

[11] Patent Number: 6,046,380
[45] Date of Patent: Apr. 4, 2000

[54] FACTOR IX PRODUCTION IN TRANSGENIC NON-HUMAN MAMMALS AND FACTOR IX DNA SEQUENCES WITH MODIFIED SPLICE SITES

[75] Inventor: Anthony John Clark, Midlothian, United Kingdom

[73] Assignee: PPL Therapeutics (Scotland) Limited, Midlothian, United Kingdom

[21] Appl. No.: 08/742,877

[22] Filed: Nov. 1, 1996

Related U.S. Application Data

[63] Continuation of application No. PCT/GB95/00996, May 2, 1995.

[30] Foreign Application Priority Data

May 3, 1994 [GB] United Kingdom .................. 9408717

[51] Int. Cl.[7] .......................... A01K 67/027; C12P 21/00; C12P 21/04; C07H 21/04
[52] U.S. Cl. ................................ 800/14; 800/7; 435/69.6; 435/212; 536/23.2; 536/23.5
[58] Field of Search ............................... 800/2; 536/23.1; 435/320.1

[56] References Cited

FOREIGN PATENT DOCUMENTS

92/11358  12/1997  WIPO.

OTHER PUBLICATIONS

Jallat et al (1990) EMBO J. 9, 3295–3301.
Archibald, A.L. et al., "High–level expression of biologically active human $\alpha_1$–antitrypsin in the milk of transgenic mice," *Proc. Natl. Acad. Sci. USA* 87:5178–5182 (1990).
Bayna, E.M. and J.M. Rosen, "Tissue–specific, high level expression of the rat whey acidic protein gene in transgenic mice," *Nucl. Acids Res.* 18(10):2977–2985 (1990).
Bischoff, R. et al., "A 17.6 kbp region located upstream of the rabbit WAP gene directs high level expression of a functional human protein variant in transgenic mouse milk," *FEBS Letters* 305(3):265–268 (1992).
Bleck, G.T. and R.D. Bremel, "Variation in Expression of a Bovine $\alpha$–Lactalbumin Transgene in Milk of Transgenic Mice," *J. Dairy Sci.* 77:1897–1904 (Jul. 1994).
Brem, G. et al., "Expression of synthetic cDNA sequences encoding human insulin–like growth factor–1 (IGF–1) in the mammary gland of transgenic rabbits," *Gene* 149:351–355 (Nov. 1994).
Bühler, Th.A. et al., "Rabbit $\beta$–Casein Promoter Directs Secretion of Human Interleukin–2 into the Milk of Transgenic Rabbits," *Bio/Tech.* 8:140–143 (1990).
Carver, A.S. et al., "Transgenic Livestock as Bioreactors: Stable Expression of Human Alpha–1–Antitrypsin by a Flock of Sheep," *Bio/Tech.* 11:1263–1270 (Nov. 1993).
Clark, A.J. et al., "Expression of Human Anti–Hemophilic Factor IX in the Milk of Transgenic Sheep," *Bio/Tech.* 7:487–492 (1989).

Devinoy, E. et al., "High level production of human growth hormone in the milk of transgenic mice: the upstream region of the rabbit whey acidic protein (WAP) gene targets transgene expression to the mammary gland," *Transgenic Res.* 3:79–89 (Mar. 1994).
DiTullio, P. et al., "Production of Cystic Fibrosis Transmembrane Conductance Regulator in the Milk of Transgenic Mice," *Bio/Tech.* 10:74–77 (1992).
Dobrovolsky, V.N. et al., "Human $\gamma$–interferon expression in the mammary gland of transgenic mice," *FEBS Letters* 319(1,2):181–184 (Mar. 1993).
Drohan, W.N. et al., "Inefficient processing of human protein C in the mouse mammary gland," *Transgenic Res.* 3:355–364 (Nov. 1994).
Ebert, K.M. et al., "Transgenic Production of a Variant of Human Tissue–Type Plasminogen Activator in Goat Milk: Generation of Transgenic Goats and Analysis of Expression," *Bio/Tech.* 9:835–838 (1991).
Ebert, K.M. et al., "Induction of Human Tissue Plasminogen Activator in the Mammary Gland of Transgenic Goats," *Bio/Tech.* 12:699–702 (Jul. 1994).
Gordon, K. et al., "Production of Human Tissue Plasminogen Activator in Transgenic Mouse Milk," *Bio/Tech.* 5:1183–1187 (1987).
Greenberg, N.M. et al., "Expression of biologically active heterodimeric bovine follicle–stimulating hormone in milk of transgenic mice," *Proc. Natl. Acad. Sci. USA* 88:8327–8331 (1991).
Hansson, L. et al., "Expression and Characterization of Biologically Active Human Extracellular Superoxide Dismutase in Milk of Transgenic Mice,"*j. Biol. Chem.* 269:5358–5363 (Feb. 1994).
Hochi, S.–I. et al., "Secretion of Bovine $\beta$–Lactalbumin Into the Milk of Transgenic Rats," *Mol. Repro & Develop.* 33: 160–164 (1992).
Hurwitz, D.R. et al., "Specific combinations of human serum albumin introns direct high level expression of albumin in transfected COS cells and in the milk of transgenic mice," *Transgenic Res.* 3: 365–375 (Nov. 1994).
Krimpenfort, P. et al., "Generation of Transgenic Dairy Cattle Using 'In Vitro' Embryo Production," *Bio/Tech.* 9:844–847 (1991).

(List continued on next page.)

*Primary Examiner*—Deborah Crouch
*Attorney, Agent, or Firm*—Sterne, Kessler, Goldstein & Fox P.L.L.C.

[57] ABSTRACT

Poor expression yields of recombinant human factor IX are attributable to aberrant splicing in heterologous expression systems such as transgenic hosts for example, transgenic nonhuman mammal The aberrant splicing sites have been identified as (a) a donor site including mRNA nucleotide 1085; and (b) an acceptor site including mRNA nucleotide 1547; adopting the mRNA nucleotide numbering of FIG. 2 of the drawings. Improved factor IX expression sequences have at least one of these sites engineered out, so as to prevent or reduce the effect of aberrant splicing and to increase yields. The improved DNA sequences may also be useful in gene therapy.

13 Claims, 10 Drawing Sheets

OTHER PUBLICATIONS

Maga, E.A. et al., "Expression of human lysozyme mRNA in the mammary gland of transgenic mice," *Transgenic Res.* 3:36–42 (Jan. 1994).

Maschio, A. et al., "Transgenic mice carrying the guinea–pig α–lactalbumin gene transcribe milk protein genes in their sebaceous glands during lactation," *Biochem. J.* 275:459–467 (1991).

Meade, H. et al., "Bovine Alpha$_{s1}$1Casein Gene Sequences Direct High Level Expression of Active Human Urokinase In Mouse Milk," *Bio/Tech.* 8:443–446 (1990).

Persuy, M.–A. et al., "High expression of the caprine β–casein gene in transgenic mice," *Eur. J. Biochem.* 205:887–893 (1992).

Pittius, C.W. et al., "A milk protein gene promoter directs the expression of human tissue plasminogen activator cDNA to the mammary gland in transgenic mice," *Proc. Natl. Acad. Sci. USA* 85:5874–5878 (1988).

Platenburg, G.J. et al., "Expression of human lactoferrin in milk of transgenic mice," *Transgenic Res.* 3:99–108 (Mar. 1994).

Reddy, V.B. et al., "Expression of Human Growth Hormone in the Milk of Transgenic Mice," *Animal Biotech.* 2(1):15–29 (1991).

Rokkones, E. et al., "Human Parathyroid Hormone as a Secretory Peptide in Milk of Transgenic Mice," *J. Cell. Biochem.* 59:168–176 (Oct. 1995).

Shani, M. et al., "Expression of human serum albumin in the milk of transgenic mice," *Transgenic Res.* 1:195–208 (1992).

Simons, J.P. et al., "Alteration of the quality of milk by expresion of sheep β–lactoglobulin in transgenic mice," *Nature* 328:530–532 (1987).

Simons, J.P. et al., "Gene Transfer into Sheep," *Bio/Tech.* 6:179–183 (1988).

Soulier, S. et al., "Expression analysis of ruminant α–lactalbumin in transgenic mice: developmental regulation and general location of important cis–regulatory elements," *FEBS Letters* 297:13–18 (1992).

Stinnakre, M.G. et al., "The bovine α–lactalbumin promoter directs expression of ovine trophoblast interferon in the mammary gland of transgenic mice," *FEBS Letters* 284(1):19–22 (1991).

Tomasette, C. et al., "Breast Cancer Protein PS2 Synthesis in Mammary Gland of Transgenic Mice and Secretion into Milk," *Mol. Endocrinol.* 3:1579–1584 (1989).

Velander, W.H. et al., "Production of Biologically Active Human Protein C in the Milk of Transgenic Mice," *Annals N.Y. Acad. Sci.* 665:391–403 (1992).

Velander, W.H. et al., "High–level expression of a heterologous protein in the milk of transgenic swine using the cDNA encoding human protein C," *Proc. Natl. Acad. Sci. USA* 89:12003–12007 (1992).

Vilotte, J.–L. et al., "Efficient tissue–specific expression of bovine α–lactalbumin in transgenic mice," *Eur. J. Biochem.* 186:43–48 (1989).

Wall, R.J. et al., "High–level synthesis of a heterologous milk protein in the mammary glands of transgenic swine," *Proc. Natl. Acad. Sci. USA* 88:1696–1700 (1991).

Wall, R.J. et al., "Synthesis and secretion of the mouse whey acidic protein in transgenic sheep," *Transgenic Res.* 5:67–72 (Jan. 1996).

Whitelaw, C.B.A. et al. , "Targeting expression to the mammary gland: intronic sequences can enhance the efficiency of gene expression in transgenic mice," *Transgenic Res.* 1:3–13 (1991).

Wright, G. et al., "High Level Expression of Active Human Alpha–1–Antitrypsin in the Milk of Transgenic Sheep," *Bio/Tech.* 9:830–834 (1991).

Yarus, S. et al., "Production of active bovine tracheal antimicrobial peptide in milk of transgenic mice," *Proc. Natl. Acad. Sci. USA* 93: 14118–14121 (Nov. 1996).

Yull, F. et al., "Fixing human factor IX (fIX): Correction of a cryptic RNA splice enables the production of biologically active fIX in the mammary gland of transgenic mice," *Proc. Natl. Acad. Sci. USA* 92:10899–10903 (Nov. 1995).

Solera, J. et al., "Factor IX$_{Madrid\ 2}$: A Deletion/Insertion in Factor IX Gene Which Abolishes the Sequence of the Donor Junction at the Exon IV–Indron d Splice Site," *Am. J. Hum. Genet.* 50:434–437 (1992).

Anson, D. S. et al., "The gene structure of human anti–haemophilic factor IX," *EMBO J.* 3(5):1053–1060 (1984).

Chen, S.–H. et al., "Splice junction mutations in factor IX gene resulting in severe hemophilia B," *Nucl. Acids Res.* 19(5):1172 (1992).

Simons, J. P. et al., "Expression of Active Human Antihemophilic Factor IX in the Milk of Transgenic Sheep," *J. Cell. Biochem. Suppl.* 12B:195 Abstr. No. H 226 (1988).

```
         M  Q  R  V  N  M  I  M  A  E  S  P  G  L  I  T  I  C  L  L  G  Y  L  L  S  A  E  C  T  V
         -46                      -40                      -30                      -20
ACCACUUUCACAACUUCGUAGCAGAGGUUAUGCAGGCGUGAACAGGAUCAUGCCAGAACACCAGGCCUCACCAUCUGCCAUCUACUCAGGCAUCCUGCUUUUAGGAUAUCUGCUAAUUGCAGUUU
         10          20          30          40          50          60          70          80          90         100         110         120

F  L  D  H  E  N  A  N  K  I  L  N  R  P  K  R  Y  N  S  G  K  L  E  E  F  V  Q  G  N  L  E  R  E  C  M  E  E  K  C  S
                    -10                      1                       *       *  10                              *   *   *
UUCUGAUCAUGAAAUGGAACGCCAACAAGAUUCUGAAUCGGCCAAAGAGGUAUAAUUCAGGGAAGCUAGAAGAGUUUGUGCAGGGAAACCUGGAACGUGAAUGCAUGGAAGAAAAGUGUAGUU
         130         140         150         160         170         180         190         200         210         220         230         240

F  E  E  A  R  E  V  F  E  N  T  E  R  T  T  E  F  W  K  Q  Y  V  D  G  D  D  Q  C  E  S  N  P  C  L  N  G  G  S  C  K  D
  *   *       *                                                              50                                     60             •
UUGAAGAAGCACGAGAAGUUUUCGAAAAUACACGAGAGAACAACUGAAUUUUGGAAGCAGUACGUUGAUGGAGAUGAUCAGUGUGAGAGUAACCCCUGCCUUAAUGGCGGCAGCUGCAAGGAUG
         250         260         270         280         290         300         310         320         330         340         350         360

D  I  N  S  Y  E  C  W  C  P  F  G  F  E  G  K  N  C  E  L  D  V  T  C  N  I  K  N  G  R  C  E  Q  F  C  K  N  S  A  D
         70                                      80                                      90                                    100
ACAUUAAUUCCUAGCGAAUGCUGGUGUCCCUUUGGAUUUGAAGGGAAGAACUGUGAAUUAGACGUCACAUGUAACAUUAAGAAUGGACGGUGUGAGCAGUUUUGUAAAAAUAGUGCUGAUA
         370         380         390         400         410         420         430         440         450         460         470         480

N  K  V  V  C  S  C  T  E  G  Y  R  L  A  E  N  Q  K  S  C  E  P  A  V  P  F  P  C  G  R  V  S  V  S  Q  T  S  K  L  T
             110                                     120                                     130                                    140
ACAAGGUGGUUUGCUCCUGUACGGAGGGAUAUCGACUUGCAGAAAACCAGAAAUCAUGCGAGCCUGCUGUUCCAUUCCCAUGUGGAAGAGUUUCUGUCUCACAAACCUCUAAGCUCACCC
         490         500         510         520         530         540         550         560         570         580         590         600
```

FIG. 2A 150                    160  ■           170            180↓
          R  A  E  A  V  F  P  D  V  D  Y  V  N  S  T  E  A  E  T  I  L  D  N  I  T  Q  S  F  N  D  F  T  R▼ V  V  G  G
          GUGGCUGAGGCUGUUUUCCUGAUGUGACUACAUGUAAAUCUACGAAGCUGAAACACCAAUCAAAGACACUCGGGUCUUGGUGGAG
             610          620         630        640          650         660         670         680          690          700        710         720

190                    200                   210                      220▼
          E  D  A  K  P  G  Q  F  P  W  Q  V  V  L  D  G  K  V  N  A  F  C  G  G  S  I  V  N  E  K  W  I  V  T  A  A  H  C  V  E
          AAGAUGGCCAAACCAGGUCAAUUCCCUGGCAGGUGGUUUUGGAUGGCAAGGUAAAUGCAUUCUGCGAGGAGGCAGCAUUGUAAACGAGAAAUGGAUGGUUACCGCUGCCCACUGUGUGGAA
             730          740          750         760           770          780        790        800          810          820        830         840

230                     240                   250
          T  G  V  K  I  T  V  V  A  G  E  H  N  I  E  E  T  H  T  E  Q  K  R  N  V  I  R  I  I  P  H  H  N  Y  N  A  A  I  N
          CUGGUGUGAAAAUUACAGUGUCCAGGCAGAGCAUAAUAUAGAGGAGACACAGAAGCGCAAAUGUGAAUCGAAUCAGCUAUAAUAA
             850          860          870          880         890           900          910          920         930         940         950        960

▼270                     280                     290                     300
          K  Y  N  H  D  I  A  L  L  E  L  D  E  P  L  V  L  N  S  Y  V  T  P  I  C  I  A  D  K  E  Y  T  N  I  F  L  K  F  G  S
          AGUACAACCAUGAUCGCCCUUCUGGAACUGACGAACCCCUUAGUCUGAACAGCUGAAACAGGAAUACACGAACACUCUCCAAAUUGGAUCUG
            970           980          990         1000         1010         1020          1030        1040          1050        1060         1070       1080

330                      340
          G  Y  V  S  G  W  G  R  V  F  H  K  G  R  S  A  L  V  L  Q  Y  L  R  V  P  L  V  D  R  A  T  C  L  R  S  T  K  F  T  I
          GCUAUGUAAGUGGCUGGGAAGAGUCUUCCACAAAGGGAGACAGCAGCCUUAGUCCUACAGUACCUUAGAGUCCCACUGGUCGACCGAGCCACAUGCCUUCGAUCUACAAAGUUCACCAUCU
            1090          1100         1110         1120          1130         1140         1150          1160         1170         1180         1190      1200

```
CAUCAUUCGUAUACUUCUGUACACAGUUAUACAUGUCUAUCAAACCCAGACUGCUAUUUCAGAACAUUGCUUCCAUAGGGACUUGCUUUUCAGAACAUAGGGAUAGGGAUAGGUAGCAAGUAAGGUGCCUGAAAAGUUUGGG
       2050        2060        2070        2080        2090        2100        2110        2120        2130        2140        2150        2160

GGAAAAGUUCUUUCAGAGAGUUAUAAGUUAUAUUUAUAUAUAUAUAUAUAAUAUAUACAAUAUAAAUAUAUAAUAUAGUGUGUGUGUAUGGCGUGUGUGUAGACACACGCAU
       2170        2180        2190        2200        2210        2220        2230        2240        2250        2260        2270        2280

ACACACAGUUGUACUCUAAUCUAGAGCCAUUGUAUGGAGCUGGACUAGGCAUGCAGAUUUGACCAAGGCAAGAUGGCAUAUCAUGUAACUAAAAAGCUGACAUU
       2290        2300        2310        2320        2330        2340        2350        2360        2370        2380        2390        2400

GACCCAGACAUAUGUACUCUUUCUAAAAUAAUAAUGCUAACAGAGAACCGUUCAAUGCAAUCUACAGCAGCGUUGCAAUCUACAGAGACUUUGAGGAAGAAUUCAACAGUGUGUC
       2410        2420        2430        2440        2450        2460        2470        2480        2490        2500        2510        2520

UUCAGCAGUUCAGAGCCAAGCAACUAAGUGUCCUUCUCCUUUAACUAGCAUCAUGUCUCCGAAGUGGAGAAGGUCCAGCAGGCUCAAAGGCA
       2530        2540        2550        2560        2570        2580        2590        2600        2610        2620        2630        2640

UAAGUCAUUCCAAUCAGCUACCUAAGUGUCGUUCCAUGGAACAUUUGAAUCCUUCUAUCUUGAAUCUUCUAUCUUGAUGUAAUCCUCUAUCUUGACUUCUAGAGAGUGCUGACCAACUGAC
       2650        2660        2670        2680        2690        2700        2710        2720        2730        2740        2750        2760

GUAUGUUUCCCUUGUGAAUUAAUAAACUGGUGUUCGGUUCpolyA
       2770        2780        2790        2800
```

FIG.2D

```
         305         415                      1550
       . S  G  Y  V  S     G        T  *
       AUCUGGCUAGUAAGUGG ——— ACUUAA ——— UUCUCUUUACAGGGGAGAA . . FIX
                  1090

AUCUGGCUAU ‐ ‐ ‐ ‐ ‐ GGGAGAA . . BIX

GURAGU                    YYYYYNCAG    CONSENSUS
```

FACTOR IX PRODUCTION IN TRANSGENIC NON-HUMAN MAMMALS AND FACTOR IX DNA SEQUENCES WITH MODIFIED SPLICE SITES

This is a continuation of International Application PCT/GB95/00996, having an international filing date of May 2, 1995.

FIELD OF THE INVENTION

This invention relates to DNA sequences encoding human factor IX (fIX). Such sequences are useful in expression systems for factor IX, including transgenic animals, and also have potential in gene therapy.

BACKGROUND OF THE INVENTION

It is difficult to achieve high expression yields of factor IX in heterologous, particularly transgenic, systems. For example, while the basic approach to β-lactoglobulin-driven transgenic expression of human factor IX in the milk of transgenic animals such as sheep (as disclosed in WO-A-8800239) does work, the yields obtained are low. There seem to have been two main reasons for this:

Failure to Express

The use of factor IX cDNAs has generally proved a problem in terms of getting reasonable levels of the appropriate fIX transcript. This problem was partially solved by the transgene rescue approach (described in WO-A-9211358, "Increased Expression by a Second Transferred Sequence in Transgenic Organisms"). In this prior publication, cointegration of β-lactoglobulin (BLG) with the human factor IX-encoding construct FIXD led to the production of lines of mice expressing high levels of FIXD mRNA. The milk of these animals, however, contained very little fIX.

Aberrant Splicing

Closer inspection of the FIXD mRNA transcripts in the BLG+FIXD mice showed that they were approximately 450 bp shorter than predicted. It was surmised that these are deleted internally most probably by an aberrant splice of the mRNA (Clark et al., *Bio/Technology* 10 1450–1454 (1992)).

Splicing of human factor IX mRNA in liver cells has been discussed in *J. Biol. Chem.* 270, 5276–5281 (1994) (Kurachi et al). Here it is indicated that the presence of splicing signal sequences results in increased expression of factor IX since spliceosome complexes act to protect precursor mRNAs from random degradation before being transported out of the nucleus.

BRIEF SUMMARY OF THE INVENTION

It has now been determined that aberrant splicing is indeed a cause of low factor IX yield in heterologous or transgenic expression systems. Furthermore, and most significantly, the location of cryptic splice sites in the human gene encoding factor IX has been identified. This discovery enables factor IX-encoding DNA sequences to be engineered to avoid the observed aberrant splicing.

According to a first aspect of the present invention, there is provided DNA having a sequence encoding a protein having human factor IX activity, wherein the DNA is modified to interfere with the functioning of at least one of the following cryptic splice sites:

(a) a donor site including mRNA nucleotide 1086; and
(b) an acceptor site including mRNA nucleotide 1547;

adopting the mRNA nucleotide numbering of FIG. 2 (SEQ ID NO: 1) of the drawings.

DETAILED DESCRIPTION OF THE INVENTION

DNA in accordance with the invention makes possible much higher levels of fIX expression than hitherto described by correcting an aberrant splice of fIX sequences.

A donor site in nuclear pre-mRNA (that is, the primary transcript of the gene which exists transiently in the nucleus before splicing to generate mRNA which is exported to the cytoplasm) contains the nucleotides GU, which after splicing become the 5' terminal nucleotides of the excised intron. An acceptor site in the nuclear pre-mRNA contains the nucleotides AG, which after splicing become the 3' terminal nucleotides of the excised intron. The nucleotide numbers given in the preceding paragraph are for the G residue of the (5') donor site and the G residue of the (3') acceptor site, respectively.

Preferred DNA in accordance with the invention encodes wild-type human factor IX. However, DNA encoding variants (particularly allelic variants from a consensus sequence), conservative mutations or other proteins is also within the scope of the invention, provided that the proteins are substantially homologous with human factor IX. "Substantial homology", as is well understood in the art, may be assessed either at the protein level or the nucleic acid level. For example, at the protein level, substantial homology may be said to be present if a candidate protein exhibits amino acid homology to human factor IX at a level of at least 40, 60, 80, 90, 95 or 99%, in increasing order of preference. At the nucleic acid level, substantial homology may be said to be present if a candidate DNA sequence exhibits DNA sequence homology to human factor IX at a level of at least 80, 90, 95 or 99%, in increasing order of preference.

It will be appreciated that the invention has application to a variety of DNA sequences encoding factor IX (or another protein having factor IX activity). In particular, the invention is applicable to cDNA sequences, genomic sequences having a full complement of natural introns and "minigene" sequences, containing some but not all of the introns present in genomic DNA encoding factor IX.

There are a variety of ways in which DNA in accordance with the invention may be modified to interfere with the functioning of the cryptic donor/acceptor sites so as to prevent or at least significantly reduce aberrant splicing.

First, the intron/exon structure of the constructs could be changed, on the basis that additional introns 5' or 3' would "compete" with the cryptic splice in some way. However, this approach may be relatively complex and lead to only partial suppression of aberrant splicing.

Secondly, the cryptic donor site could be engineered out. Either the G or the U of the mRNA donor site could be replaced with another base, or both could be replaced, provided that a stop codon does not result from the change. This approach is technically simpler than the competitive intron approach described above, but necessitates a change in the amino acid sequence of factor IX, because the GU residues at the donor site form the first two nucleotides of a valine codon, and all valine codons begin GU. This may not be a disadvantage, and may actually be an advantage if a second or subsequent generation variant of factor IX is being engineered. However, it is not suitable if retention of the wild-type factor IX sequence, at least in the region of the donor site, is essential.

Thirdly, and in most instances preferably, the cryptic acceptor site can be engineered out. This site lies in the 3' untranslated region of factor IX DNA, and so there are no implications for the amino acid sequence. Either the A or the G of the mRNA acceptor site could be deleted or replaced with another base, or both could be deleted or replaced. In fact, in some of the simplest embodiments of the invention, deletion of the acceptor site just requires the production of a factor IX cDNA segment which is shortened at the 3' end (or, of course, a DNA other than a cDNA shortened correspondingly). In other embodiments, site-directed mutagenesis techniques may be used specifically to alter the acceptor site (or, of course, the donor site).

DNA in accordance with the invention is useful in systems for expressing factor IX (or like proteins).

According to a second aspect of the invention, there is provided an expression host comprising DNA in accordance with the first aspect of the invention operably linked to an expression control sequence. The expression control sequence will usually comprise a promoter, and other regulatory sequences may be present.

While the invention may be generally useful across various different cell types and cultured cells, it is with transgenic animal expression systems that the invention has particular application, because of the large yields that are in principle available from this technology. Therefore, the expression host is in certain favoured embodiments an animal, such as a mammal.

A preferred transgenic system for the production of heterologous proteins involves the use of transgenic placental non-human mammals, especially sheep and other dairy animals, which express a transgene in the mammary gland (of an adult female) under the control of a milk protein promoter, particularly that of the milk whey protein β-lactoglobulin, as disclosed in WO-A-8800239, WO-A-9005188 and WO-A-9211385.

However, the invention is not limited to the use of these preferred transgenic systems. It is expected that factor IX-encoding sequences will be used in gene therapy approaches for haemophilia, for example using retroviral vectors or direct transfection techniques into stem cells. The advantages of an improved fIX sequence which does not aberrantly splice are self evident.

Preferred features for each aspect of the invention are as for each other aspect, mutatis mutandis.

BRIEF DESCRIPTION OF THE DRAWINGS

FIGS. 2A–2D also refer to Example 1 and are adapted from Anson et al., *The EMBO Journal* 3 (5) 1053–1060 (1984) and show the locations of the cryptic donor and acceptor sites in factor IX mRNA (SEQ ID NO: 1);

FIG. 3 refers to Example 1 and shows in more detail how the donor (SEQ ID NO: 10) and acceptor (SEQ ID NO: 11) sites interact; the figure also shows generalised consensus sequences for donor and acceptor sites (SEQ ID NO: 13);

EXAMPLES

The invention will now be illustrated by the following examples.

Example 1

Aberrant Splicing of Construct FIXD

Figure 1:
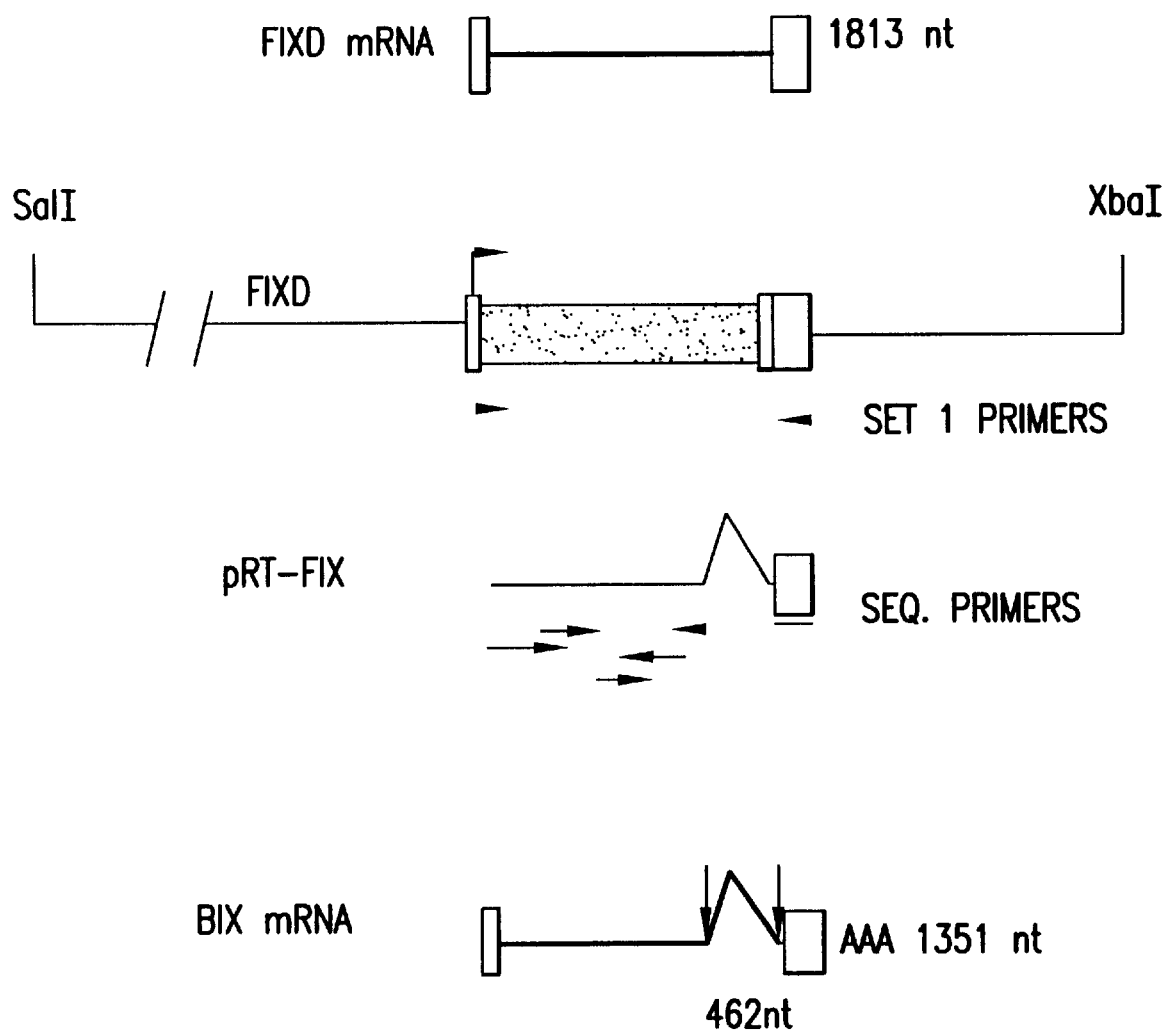
FIG. 1 refers to Example 1 and shows the scheme used to confirm, the aberrant splicing of the FIXD construct.

The aberrant splicing of the FIXD mRNA was confirmed by cloning these transcripts by RT-PCR from mammary gland RNA of one of the expressing lines of mice. FIXD is disclosed in Example 3 of WO-A-9005188 and Comparative Example 6 of WO-A-9211385 and comprises human factor IX (fIX) cDNA fused to β-lactoglobulin (BLG) 5' and 3' sequences (including exons 6 and 7); FIXD contains no naturally occurring introns. Primers (Set 1: FIG. 1) specific to the 5' end of the fIX cDNA and 3' end of BLG were designed and constructed. The primers had the following sequences:

Set 1-5'fIX (code no. 292343): 5'CAC CAA, GCT TCA TCA CCA TCT GCC 3' *(SEQ ID NO: 4)

Set 1-3'BLG (code no. 290646): 5'GGG TGA CTG CAG TCC TGG TCC C 3' (SEQ ID NO: 5)

*contains an introduced HindIII site to enable cloning.

These primers amplified the shorter FIXD transcript (named BIX) from the BLG+FIXD mice and this was cloned in plasmid vector pB$_{LUESCRIPT}$ as pRT-FIX, which was then sequenced. The sequence of pRT-FIX showed a 462 nt internal deletion in the fIX sequences. Thus instead of the 1813 nt size of predicted for FIXD mRNA the BIX transcripts were 1351 nucleotides (FIG. 1).

Figure 2C:
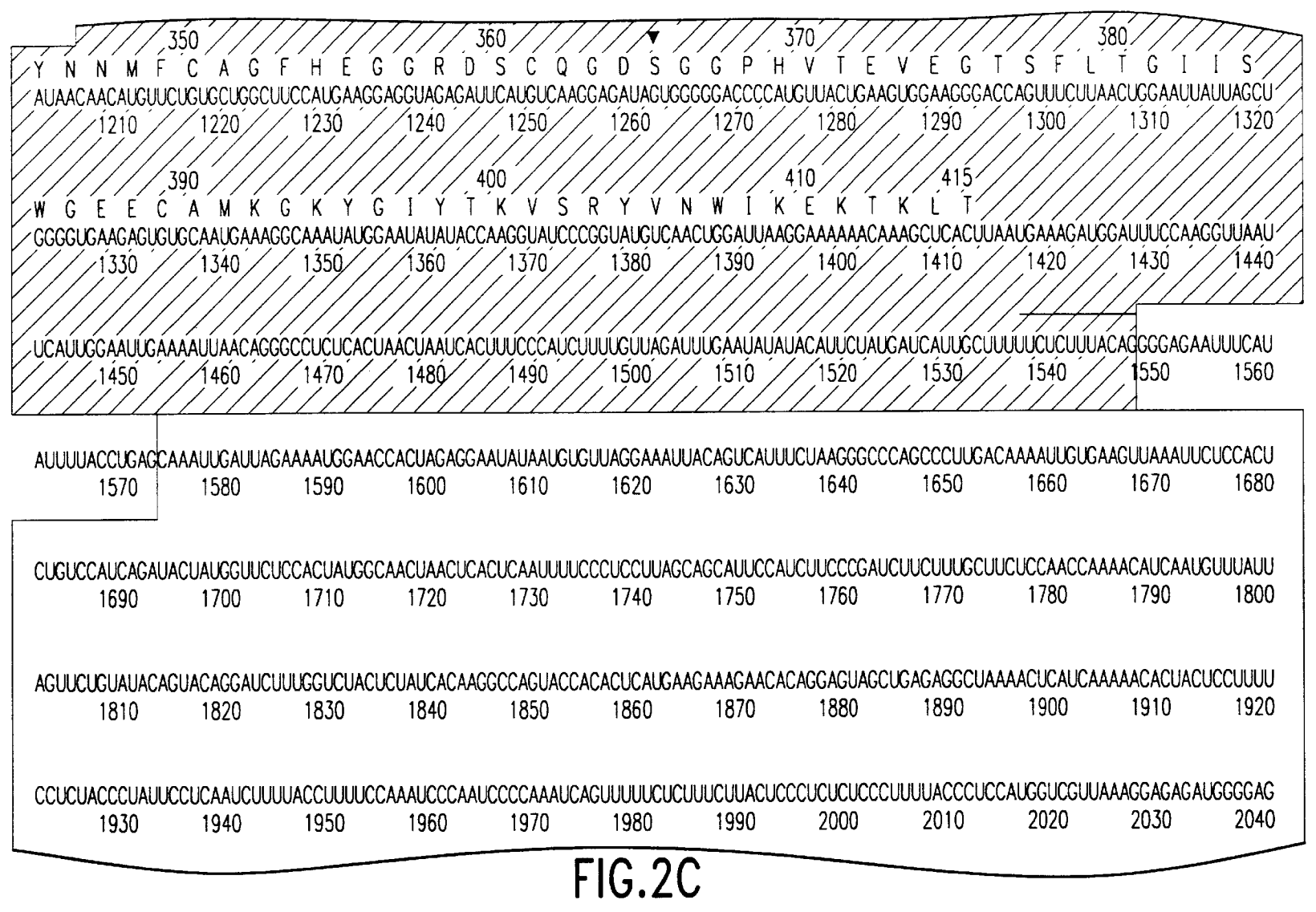

The sequence of pRT-FIX, determined by the dideoxy method of Sanger, identified the precise location of the deletion observed in BIX mRNA. Inspection of the fIX cDNA sequence (Anson et al., *The EMBO Journal* 3 (5) 1053–1060 (1984)) and comparison to the 5' and 3' break points deduced from pRT-FIX showed that the deletion was almost certainly due to aberrant splicing. Thus the deletion comprises bp 1085-1547 inclusive (as numbered in the Anson paper and in FIG. 2 (SEQ ID NO: 1) of this specification). The most 5' sequence is 5'GUAAGUGG and the most 3' sequence is UUUCUCUUAC$\underline{AG}$3' (SEQ ID NO: 14) (FIG. 3). These are very 'good' consensus sequences for the donor (5') and acceptor (3') sites of an intron. (The 5' and 3' ends of an intron must have GU and AG respectively: these are absolute requirements for splicing; the other bases here are also close to the consensus for the donor and acceptor sites.)

Figure 4:
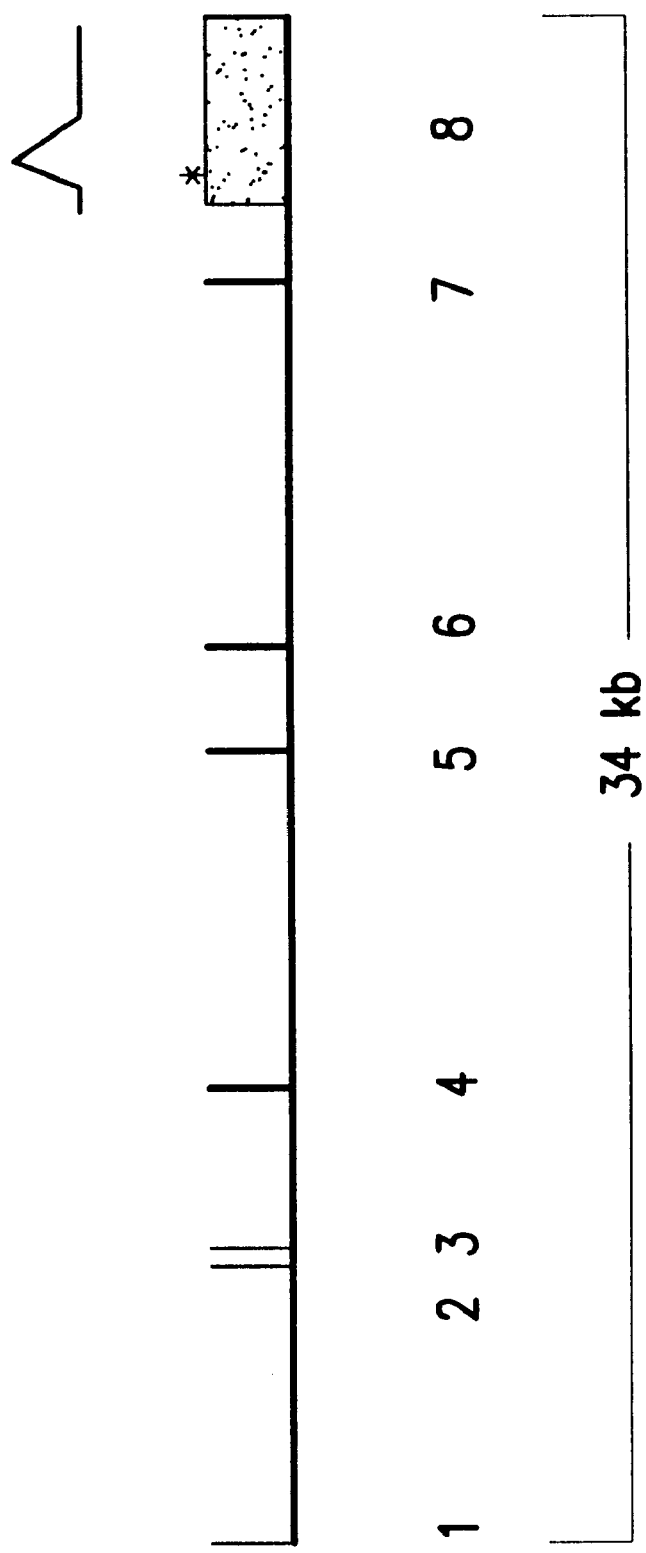
FIG. 4 shows the gross structure of the human factor IX gene, including the locations of the cryptic splice sites.

Note that the presence of donor and acceptor sites does not mean that a gene must be spliced in this way: from the sequence one cannot predict whether or not a splice will occur. Indeed in the natural factor IX gene these sites are present in the last exon (exon 8) separated by the same sequences that are in FIXD (FIG. 4). Nevertheless these sites are not used in the normal expressing factor IX pre-mRNA in human liver. Thus, for some reason the FIX transcripts produced in the mammary gland use these cryptic splice sites, resulting in the production of the internally deleted BIX mRNA. This internally deleted mRNA cannot code for a functional fIX protein since it results in the removal of segment coding for the last 109 amino acids of fIX.

Example 2

Aberrant Splicing Occurs with Other fIX Constructs

Figure 5:
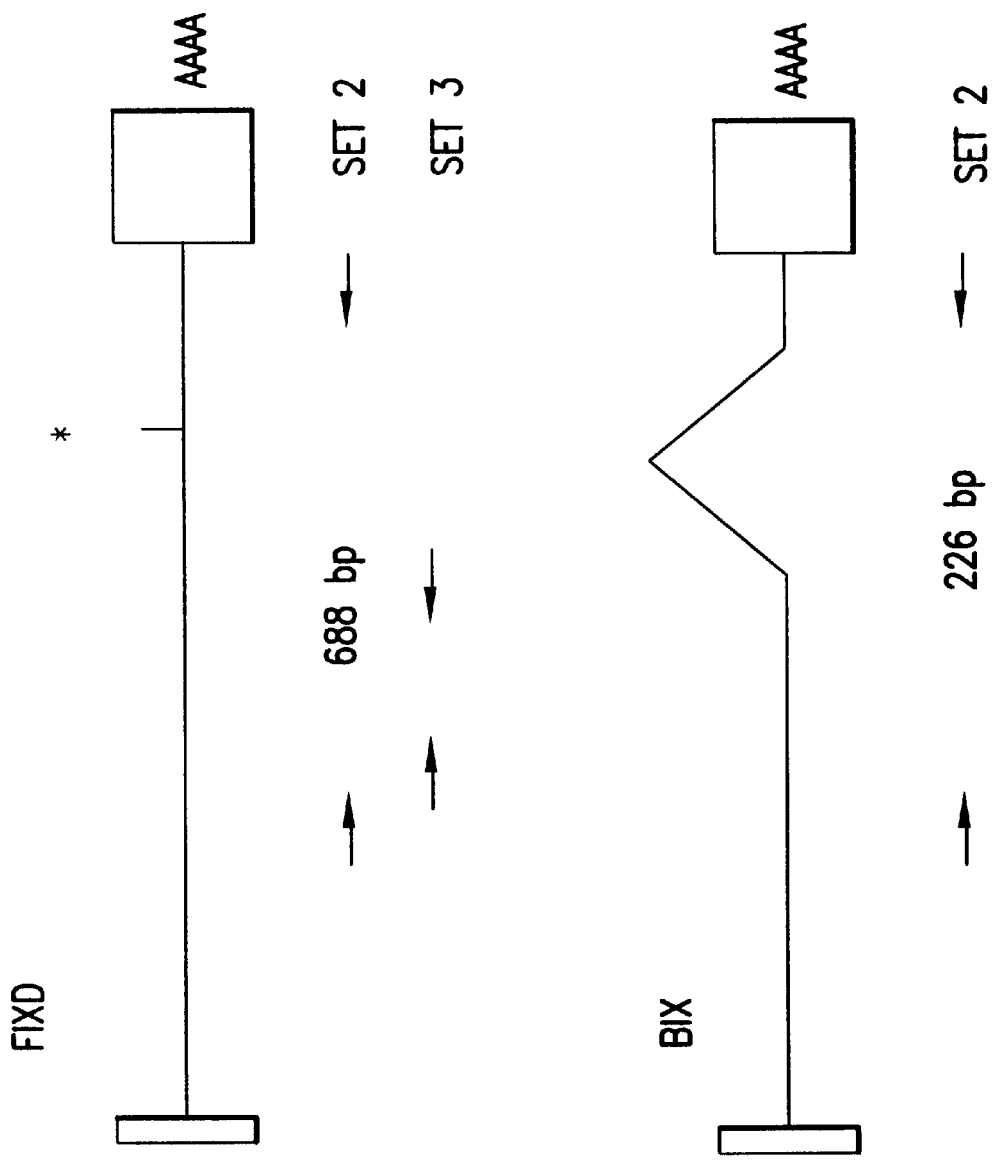
FIG. 5 refers to Example 2 and shows a PCR-based scheme for distinguishing between unspliced and aberrantly spliced mRNA for different constructs and in different expression systems.

The identification of the aberrant splicing of fIX cDNA sequences was made with mice expressing the FIXD construct (cointegrated with BLG). Transgenic sheep with fIX cDNA sequences had previously been made, but in these sheep the fIX cDNA sequences were integrated into the first exon of the intact BLG gene, as a construct called FIXA (as described in Example 3 of WO-A-8800239). This construct also appeared to behave rather poorly and produced rather low levels of fIX in the milk. It was, therefore, also of interest to see whether this aberrant splice occurred in the mammary gland with this fIX construct. Mammary RNA samples from sheep carrying another relatively poorly expressing construct, JFIXA1 (identified as J FIX A 1 in Section E of Example 4 of WO-A-9005188), were also procured from transgenic sheep derived from a founder transgenic prepared as disclosed in WO-A-9005188. A set of PCR primers (Set 2: FIG. 5) were designed which upon RT-PCR amplification of RNA would distinguish the unspliced fIX sequences from the aberrantly spliced mRNA that was observed for BIX mRNA. In wild type (non-aberrantly spliced mRNA) these primers would generate a 689 p fragment, whereas in aberrantly spliced mRNA they would generate a 227 bp fragment. These primers had the following sequences:

Set 2-5'fIX (code no. 795X): 5'GAG GAG ACA GAA CAT ACA GAG C 3' (SEQ ID NO: 6)

Set 2-3'fIX (code no. 794X): 5'CAG GTA AAA TAT GAA ATT CTC CC 3' (SEQ ID NO: 7)

and were used against a variety of RNA prepared from tissues expressing fIX. The results are shown in Table 1.

TABLE 1

| RNA | PCR Fragment | Splice | Comment |
| --- | --- | --- | --- |
| Human liver | 689 | no | normal splicing |
| Control m. mammary | N/A | N/A | no fIX expression |
| Control s. mammary | N/A | N/A | no fIX expression |
| BIX (FIXD + BLG) | 227 | yes | confirms sequence |
| FIXA: sheep mam | 227 | yes | aberrant splice also |
| FIXA: mouse mam | 689 | no | splice not observed |
| JFIXA1: sheep mam | 227 | yes | aberrant splice also |

FIXA and JFIXA1 in sheep mammary gland do show the same aberrant splice as BIX, therefore it is not strictly construct dependent. FIXA in mouse does, however, present a rather confusing situation. Only 1/12 mice expressed this construct, but at relatively high levels (30 μ/ml). The mouse clearly does not carry out this aberrant splice in the mammary gland and hence quite high levels of fIX in milk are seen. But why this happens in this one mouse is not understood. Nevertheless it suggests that the absence of the aberrant splice can improve fIX levels in milk.

Example 3

Construction of FIX-Δ3' Splice

Figure 6:
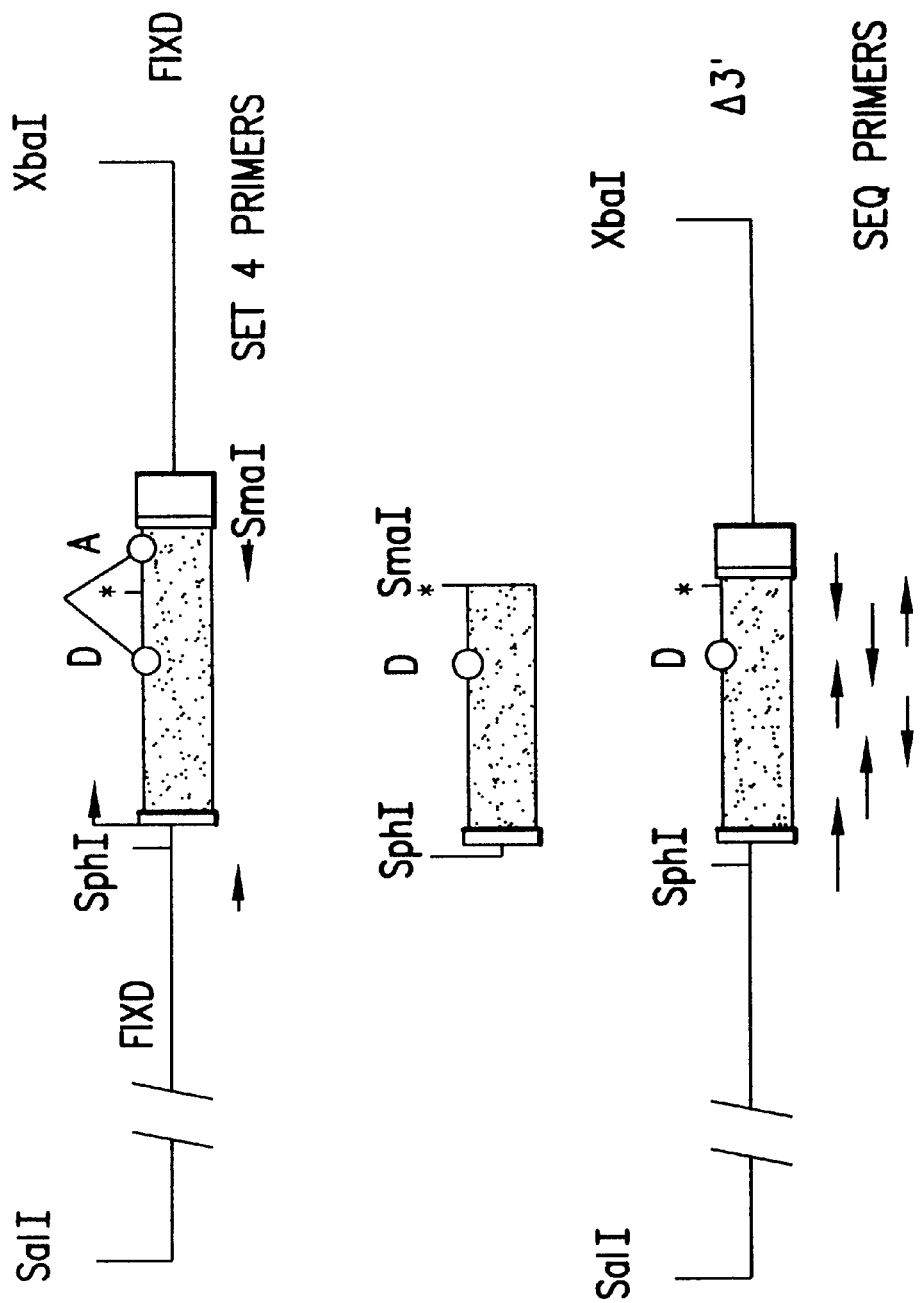
FIG. 6 refers to Example 3 and shows the construction of a construct designated FIXD-Δ3' splice.

This construction is outlined in FIG. 6. A set of PCR primers (set 4)

Set 4 5'BLG (976G) 5'GCT TCT GGG GTC TAC CAG GAA C 3' (SEQ ID NO: 8)

Set 4 3'fIX (2212) 5'TAT AAC CCG GGA AAT CCA TCT TTC ATT AAG T 3' (SEQ ID NO: 9) *

*contains additional 5' sequence including new SmaI site for cloning purposes. were used to amplify a segment of FIXD from the 5' BLG sequence to a sequence just 3' to the stop codon of fIX but 5' to the cryptic acceptor splice site. This segment of DNA thus contains the coding sequence of fIX but lacks the cryptic acceptor site in the 3' untranslated region. This segment was fused to BLG sequences to make a construct very similar to FIXD but lacking 141 bp of 3' flanking sequences of fIX present in FIXD, including the cryptic acceptor site.

Example 4

Expression of FIX-Δ3' Splice

To test whether FIX-Δ3' splice resulted in improved fIX expression in transgenic animals it was coinjected with BLG into mouse eggs (as per WO-A-9211385) and a number of is transgenic lines established. Expression of the FIX-Δ3' splice transgene was analysed in the mammary gland at the RNA and protein level.

Protein analysis

Nine lines of transgenic mice have so far been analysed. All of them exhibit detectable levels of fIX in milk. One of them (line 31) showed very high levels (an average of 60.9 μg/ml) with some individuals showing >100 μg/ml (Table 2): this is by far the highest level of fIX ever achieved in milk.

ELISA Analysis of Factor IX Milk Samples

These milks were from transgenic mice with the modified factor IX cDNA (acceptor splice site removed). The ELISA is based on capture by a rabbit polyclonal and detection is by the same polyclonal but modified by biotinylation. Expression is indicated below:

TABLE 2

RNA and Protein Expression in FIXΔ3' Lines

| Line | Copy Nos.* BLG/FIXΔ3 | RNA (ng/μg)@ | Protein μg/μl+ |
| --- | --- | --- | --- |
| 3 | nd | + | 2.9 (2) |
| 11 | 8/2 | +(.04) | 4.2 (3) |
| 12 | 15/2 | +(.02) | 9.1 (8) |
| 14 | 14/3 | − | 0.3 (1) |
| 23 | 28/3 | − | 0.4 (2) |
| 31 | 6/2 | +(.44) | 60.9 (18)$ |
| 34 | 9/1 | − | 0.38 (3) |
| 41 | 6/1 | − | <0.1 (2) |
| 44 | nd | + | 0.6 (3) |

Figure 7:
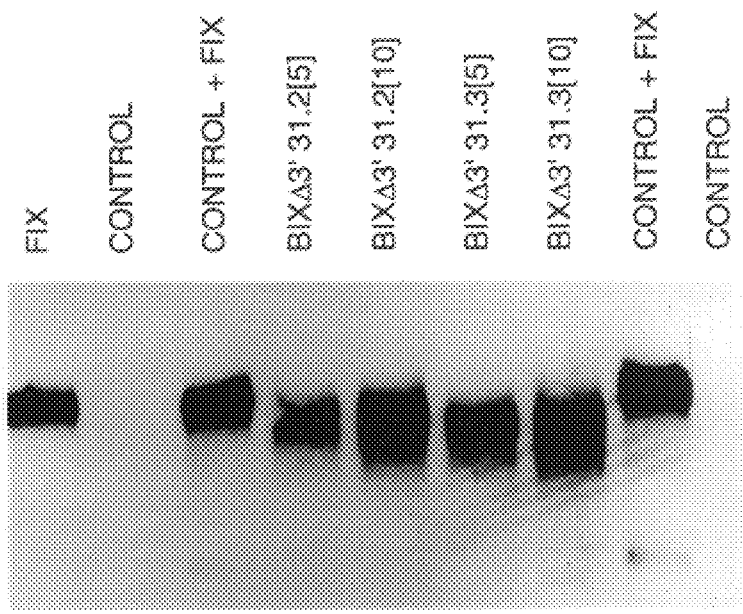
FIG. 7 refers to Example 4 and shows a Western Blotting analysis of milk from transgenic mice expressing high yields of human factor IX. Milk samples from two animals from line FIXDΔ3'-splice (31 31.2 and 31.3) were electrophoresed under non-reducing conditions. Milk samples were diluted 1/200 and either 5 µl or 10 µl loaded. fIX, 10 ng fIX; CM, control milk; CM+fIX, control milk+10 ng fIX.

*estimated by PhosphorImager analysis of S. blots of tail DNA; these values are approximate ("nd" indicates "not done")
@in some samples the level of FIXDΔ3' mRNA was estimated relative to an *in vitro* transcribed fIX transcript
+measured by ELISA; averaged from the number of G$_1$ (first generation) or G$_2$ (second generation) samples shown in parentheses
$fIX levels exceeded 100 μg/ml in some individuals of this line Furthermore, the protein produced has a very similar mobility to normal plasma derived human fIX on reducing and non-reducing gels (FIG. 7) and is biologically active (Table 3). These levels of fIX production would be commercial in sheep.

Purification and Biological Activity of Human fIX from Transgenic Mouse Milk fIX was purified from pooled mouse milks from line 31 by immunoaffinity chromatography. MabA7 which binds the Ca+ binding fIX Gla domain was a kind gift from Charles Lutsch. The antibody was coupled to cyanogen bromide activated Sepharose. Diluted milk was incubated overnight with antibody-conjugated Sepharose in 50 mM Tris, 150 mM NaCl pH 7.5 (TBS)+50 mM $CaCl_2$ at 4° C. Bound protein was eluted isocratically with TBS, 25 mM EDTA, pH 7.5 fIX coagulation activity was measured by the addition of fIX deficient plasma (Diagnostic Reagents, Oxon, UK) and APTT reagent (Sigma) with the reaction initiated after 5 minutes by addition of Ca+. Coagulation was measured by ball oscillation with an ST4 Analyser (Diagnostica Stago). Normal human plasma (4 μg/ml fIX as measured by ELISA) was used as standard. The results are indicated in Table 3 below:

TABLE 3

| Pooled Milk* | Eluate | | | |
|---|---|---|---|---|
| Total fIX@ (μg) | Total fIX@ (μg) | Recovery | Conc$^{n@}$ (μg/ml) | Activity+ (μg/ml) |
| 140 | 61.6 | 44% | 30.8 | 30.85 |

*a number of milk samples from line FIXΔ3'31 were pooled
@measured by ELISA
+measured by clotting assay

RNA analysis

Figure 8:
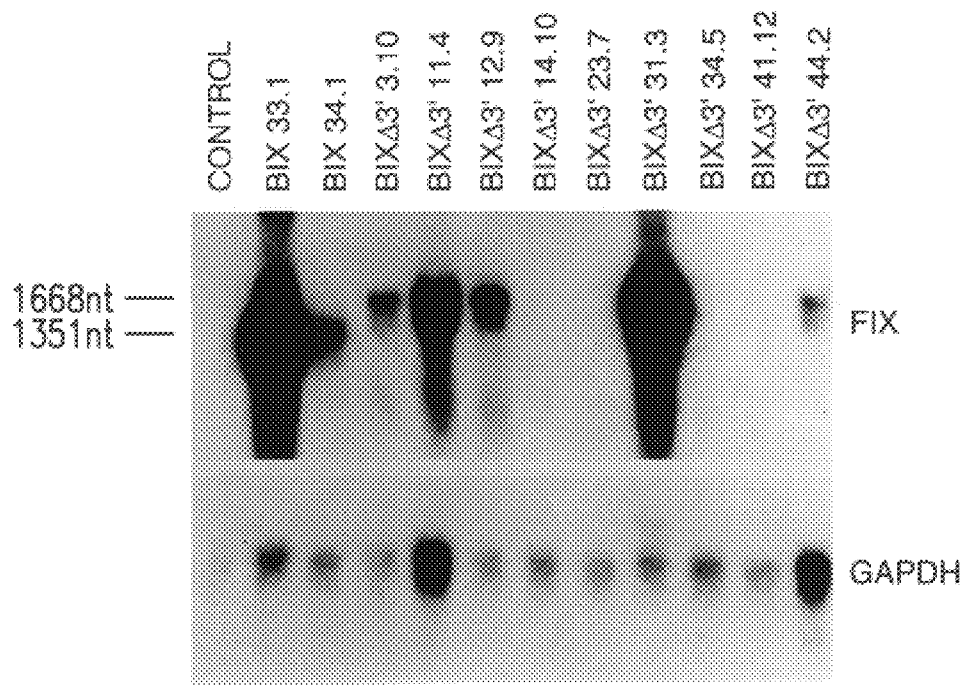
FIG. 8 also refers to Example 4 and shows Northern blots of representative RNA samples from FIXD-Δ3' splice mice probed with a factor IX-specific probe. Mammary gland RNAs from high and medium expressing BIX mice (BIX33.1 and BIX34.1) were compared to mammary gland samples from FIXDΔ3'-splice transgenic mice (labelled BIXΔ3'3.10→BIXΔ3'44.2). Blots were probed with labelled insert from p5G3'CVII a plasmid containing cDNA sequences human fIX and then reprobed with GAPDH to control for loading. The sizes of the transcripts are indicated. The FIXDΔ3'-splice transcripts are evidently larger than those from the BIX mice.

Northern blots of representative RNA samples from FIX-Δ3' splice mice were probed with a fIX-specific probe. The predicted size transcripts (~1680 nt) were observed (FIG. 8) and, furthermore, the steady state mRNA levels correlated with the levels of fIX detected in milk (eg line 31 had the highest mRNA levels (see Table 2)). These FIX-Δ3' splice RNAs were co-run with some BIX RNAs. Note that they have a higher molecular weight than the BIX mRNA (1351 nt) even though the construct is smaller. The aberrant splice which shortens BIX mRNA has now been cured. This was confirmed by an RT-PCR analysis of FIX-Δ3' splice RNA which showed that the 3' segment of the transcript was intact (not shown).

I claim:

1. A DNA encoding a biologically active human factor IX, wherein the DNA is modified at least one of the following cryptic splice sites:

(a) a donor site including mRNA nucleotide 1086; and (b) an acceptor site including mRNA nucleotide 1547; adopting the mRNA nucleotide numbering of SEQ ID NO: 1, such that the function of at least one of said splice sites is inhibited, and wherein the DNA encodes a biologically active human factor IX.

2. DNA as claimed in claim 1, wherein said DNA encodes a biologically active human factor IX having a wild-type amino acid sequence as shown in SEQ ID NO: 2.

3. DNA as claimed in claim 1, which comprises at least one of the introns present in genomic DNA encoding factor IX as shown in SEQ ID NO: 1.

4. DNA as claimed in claim 1, in which the cryptic donor site is engineered out.

5. DNA as claimed in claim 1, in which the cryptic acceptor site is engineered out.

6. DNA as claimed in claim 5, which is a DNA segment encoding factor IX, the DNA segment being shortened at its 3' end to delete the acceptor site.

7. DNA as claimed in claim 6, which is cDNA.

8. A non-human placental mammal whose genome comprises a DNA as claimed in claim 1 operably linked to a DNA encoding an expression control sequence, wherein said mammal expresses a detectable level of biologically active human factor IX in the milk of the mammal from said DNA.

9. The non-human placental mammal as claimed in claim 8, wherein the expression control sequence directs expression in the mammary gland so that a detectable level of biologically active human factor IX is present in the mammal's milk.

10. The non-human placental mammal as claimed in claim 9, wherein the expression control sequence comprises the β-lactoglobulin promoter.

11. A method of producing a biologically active human factor IX protein, the method comprising producing milk in the mammary gland of a non-human placental mammal whose genome comprises a DNA as claimed in claim 1 operably linked to a DNA encoding an expression control sequence, wherein expression of the DNA results in the production of a detectable level of biologically active human factor IX in the milk of the mammal.

12. A method as claimed in claim 11, further comprising collecting said milk from the mammary gland.

13. A method as claimed in claim 12, further comprising purifying the protein by immunoaffinity chromatography.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 2802 base pairs
      (B) TYPE: nucleic acid
      (C) STRANDEDNESS: single
      (D) TOPOLOGY: linear (ii) MOLECULE TYPE: mRNA (ix) FEATURE:
      (A) NAME/KEY: CDS
      (B) LOCATION: 30..1412

(ix) FEATURE:
      (A) NAME/KEY: sig_peptide
      (B) LOCATION: 30..167

(ix) FEATURE:
      (A) NAME/KEY: mat_peptide
      (B) LOCATION: 168..1412

(xi) SEQUENCE DESCRIPTION: SEQ ID NO:1:

```
ACCACUUUCA CAACUUGCUA GCAGAGGUU AUG CAG CGC GUG AAC AUG AUC AUG        53
                                Met Gln Arg Val Asn Met Ile Met
                                -46 -45                 -40

GCA GAA UCA CCA GGC CUC AUC ACC AUC UGC CUU UUA GGA UAU CUA CUC       101
Ala Glu Ser Pro Gly Leu Ile Thr Ile Cys Leu Leu Gly Tyr Leu Leu
        -35                 -30                 -25

AGU GCU GAA UGU ACA GUU UUU CUU GAU CAU GAA AAC GCC AAC AAA AUU       149
Ser Ala Glu Cys Thr Val Phe Leu Asp His Glu Asn Ala Asn Lys Ile
        -20                 -15                 -10

CUG AAU CGG CCA AAG AGG UAU AAU UCA GGU AAA UUG GAA GAG UUU GUU       197
```

-continued

```
            Leu Asn Arg Pro Lys Arg Tyr Asn Ser Gly Lys Leu Glu Glu Phe Val
                 -5               1               5                   10

CAA GGG AAC CUU GAG AGA GAA UGU AUG GAA GAA AAG UGU AGU UUU GAA            245
Gln Gly Asn Leu Glu Arg Glu Cys Met Glu Glu Lys Cys Ser Phe Glu
             15                  20                  25

GAA GCA CGA GAA GUU UUU GAA AAC ACU GAA AGA ACA ACU GAA UUU UGG            293
Glu Ala Arg Glu Val Phe Glu Asn Thr Glu Arg Thr Thr Glu Phe Trp
             30                  35                  40

AAG CAG UAU GUU GAU GGA GAU CAG UGU GAG UCC AAU CCA UGU UUA AAU            341
Lys Gln Tyr Val Asp Gly Asp Gln Cys Glu Ser Asn Pro Cys Leu Asn
             45                  50                  55

GGC GGC AGU UGC AAG GAU GAC AUU AAU UCC UAU GAA UGU UGG UGU CCC            389
Gly Gly Ser Cys Lys Asp Asp Ile Asn Ser Tyr Glu Cys Trp Cys Pro
             60                  65                  70

UUU GGA UUU GAA GGA AAG AAC UGU GAA UUA GAU GUA ACA UGU AAC AUU            437
Phe Gly Phe Glu Gly Lys Asn Cys Glu Leu Asp Val Thr Cys Asn Ile
 75              80                  85                  90

AAG AAU GGC AGA UGC GAG CAG UUU UGU AAA AAU AGU GCU GAU AAC AAG            485
Lys Asn Gly Arg Cys Glu Gln Phe Cys Lys Asn Ser Ala Asp Asn Lys
             95                 100                 105

GUG GUU UGC UCC UGU ACU GAG GGA UAU CGA CUU GCA GAA AAC CAG AAG            533
Val Val Cys Ser Cys Thr Glu Gly Tyr Arg Leu Ala Glu Asn Gln Lys
            110                 115                 120

UCC UGU GAA CCA GCA GUG CCA UUU CCA UGU GGA AGA GUU UCU GUU UCA            581
Ser Cys Glu Pro Ala Val Pro Phe Pro Cys Gly Arg Val Ser Val Ser
            125                 130                 135

CAA ACU UCU AAG CUC ACC CGU GCU GAG GCU GUU UUU CCU GAU GUG GAC            629
Gln Thr Ser Lys Leu Thr Arg Ala Glu Ala Val Phe Pro Asp Val Asp
            140                 145                 150

UAU GUA AAU UCU ACU GAA GCU GAA ACC AUU UUG GAU AAC AUC ACU CAA            677
Tyr Val Asn Ser Thr Glu Ala Glu Thr Ile Leu Asp Asn Ile Thr Gln
155             160                 165                 170

AGC ACC CAA UCA UUU AAU GAC UUC ACU CGG GUU GUU GGU GGA GAA GAU            725
Ser Thr Gln Ser Phe Asn Asp Phe Thr Arg Val Val Gly Gly Glu Asp
            175                 180                 185

GCC AAA CCA GGU CAA UUC CCU UGG CAG GUU GUU UUG AAU GGU AAA GUU            773
Ala Lys Pro Gly Gln Phe Pro Trp Gln Val Val Leu Asn Gly Lys Val
            190                 195                 200

GAU GCA UUC UGU GGA GGC UCU AUC GUU AAU GAA AAA UGG AUU GUA ACU            821
Asp Ala Phe Cys Gly Gly Ser Ile Val Asn Glu Lys Trp Ile Val Thr
            205                 210                 215

GCU GCC CAC UGU GUU GAA ACU GGU GUU AAA AUU ACA GUU GUC GCA GGU            869
Ala Ala His Cys Val Glu Thr Gly Val Lys Ile Thr Val Val Ala Gly
            220                 225                 230

GAA CAU AAU AUU GAG GAG ACA GAA CAU ACA GAG CAA AAG CGA AAU GUG            917
Glu His Asn Ile Glu Glu Thr Glu His Thr Glu Gln Lys Arg Asn Val
235             240                 245                 250

AUU CGA AUU AUU CCU CAC CAC AAC UAC AAU GCA GCU AUU AAU AAG UAC            965
Ile Arg Ile Ile Pro His His Asn Tyr Asn Ala Ala Ile Asn Lys Tyr
            255                 260                 265

AAC CAU GAC AUU GCC CUU CUG GAA CUG GAC GAA CCC UUA GUG CUA AAC           1013
Asn His Asp Ile Ala Leu Leu Glu Leu Asp Glu Pro Leu Val Leu Asn
            270                 275                 280

AGC UAC GUU ACA CCU AUU UGC AUU GCU GAC AAG GAA UAC ACG AAC AUC           1061
Ser Tyr Val Thr Pro Ile Cys Ile Ala Asp Lys Glu Tyr Thr Asn Ile
            285                 290                 295

UUC CUC AAA UUU GGA UCU GGC UAU GUA AGU GGC UGG GGA AGA GUC UUC           1109
Phe Leu Lys Phe Gly Ser Gly Tyr Val Ser Gly Trp Gly Arg Val Phe
300                 305                 310
```

```
CAC AAA GGG AGA UCA GCU UUA GUU CUU CAG UAC CUU AGA GUU CCA CUU      1157
His Lys Gly Arg Ser Ala Leu Val Leu Gln Tyr Leu Arg Val Pro Leu
315                 320                 325                 330

GUU GAC CGA GCC ACA UGU CUU CGA UCU ACA AAG UUC ACC AUC UAU AAC      1205
Val Asp Arg Ala Thr Cys Leu Arg Ser Thr Lys Phe Thr Ile Tyr Asn
                335                 340                 345

AAC AUG UUC UGU GCU GGC UUC CAU GAA GGA GGU AGA GAU UCA UGU CAA      1253
Asn Met Phe Cys Ala Gly Phe His Glu Gly Gly Arg Asp Ser Cys Gln
            350                 355                 360

GGA GAU AGU GGG GGA CCC CAU GUU ACU GAA GUG GAA GGG ACC AGU UUC      1301
Gly Asp Ser Gly Gly Pro His Val Thr Glu Val Glu Gly Thr Ser Phe
        365                 370                 375

UUA ACU GGA AUU AUU AGC UGG GGU GAA GAG UGU GCA AUG AAA GGC AAA      1349
Leu Thr Gly Ile Ile Ser Trp Gly Glu Glu Cys Ala Met Lys Gly Lys
    380                 385                 390

UAU GGA AUA UAU ACC AAG GUA UCC CGG UAU GUC AAC UGG AUU AAG GAA      1397
Tyr Gly Ile Tyr Thr Lys Val Ser Arg Tyr Val Asn Trp Ile Lys Glu
395                 400                 405                 410

AAA ACA AAG CUC ACU UAAUGAAAGA UGGAUUUCCA AGGUUAAUUC AUUGGAAUUG      1452
Lys Thr Lys Leu Thr
                415

AAAAUUAACA GGGCCUCUCA CUAACUAAUC ACUUUCCCAU CUUUUGUUAG AUUUGAAUAU    1512

AUACAUUCUA UGAUCAUUGC UUUUUCUCUU UACAGGGGAG AAUUCAUAU UUUACCUGAG     1572

CAAAUUGAUU AGAAAAUGGA ACCACUGAGG GAAUAUAAUG UGUUAGGAAA UUACAGUCAU    1632

UUCUAAGGGC CCAGCCCUUG ACAAAAUUGU GAAGUUAAAU UCUCCACUCU GUCCAUCAGA    1692

UACUAUGGUU CUCCACUAUG GCAACUAACU CACUCAAUUU UCCCUCCUUA GCAGCAUUCC    1752

AUCUUCCCGA UCUUCUUUGC UUCUCCAACC AAAACAUCAA GUUUAUUAG UUCUGUAUAC     1812

AGUACAGGAU CUUUGGUCUA CUCUAUCACA AGGCCAGUAC CACACUCAUG AAGAAAGAAC    1872

ACAGGAGUAG CUGAGAGGCU AAAACUCAUC AAAAACACUA CUCCUUUUCC UCUACCCUAU    1932

UCCUCAAUCU UUUACCUUUU CCAAAUCCCA AUCCCAAAU CAGUUUUUCU CUUUCUUACU     1992

CCCUCUCUCC CUUUUACCCU CCAUGGUCGU UAAAGGAGAG AUGGGGAGCA UCAUUCUGUU    2052

AUACUUCUGU ACACAGUUAU ACAUGUCUAU CAAACCCAGA CUUGCUUCCA UAGUGGGGAC    2112

UUGCUUUUCA GAACAUAGGG AUGAAGUAAG GUGCCUGAAA AGUUUGGGGG AAAAGUUUCU    2172

UUCAGAGAGU UAAGUUAUUU UAUAUAUAUA AUAUAUAUAU AAAAUAUAUA AUAUACAAUA   2232

UAAAUAUAUA GUGUGUGUGU GUAUGCGUGU GUGUAGACAC ACACGCAUAC ACACAUAUAA   2292

UGGAAGCAAU AAGCCAUUCU AAGAGCUUGU AUGGUUAUGG AGGUCUGACU AGGCAUGAUU   2352

UGACGAAGGC AAGAUUGGCA UAUCAUUGUA ACUAAAAAAG CUGACAUUGA CCCAGACAUA   2412

UUGUACUCUU UCUAAAAAUA AUAAUAAUAA UGCUAACAGA AAGAAGAGAA CCGUUCGUUU   2472

GCAAUCUACA GCUAGUAGAG ACUUUGAGGA AGAAUUCAAC AGUGUGUCUU CAGCAGUGUU   2532

CAGAGCCAAG CAAGAAGUUG AAGUUGCCUA GACCAGAGGA CAUAAGUAUC AUGUCUCCUU   2592

UAACUAGCAU ACCCCGAAGU GGAGAAGGGU GCAGCAGGCU CAAAGGCAUA AGUCAUUCCA   2652

AUCAGCCAAC UAAGUUGUCC UUUUCUGGUU UCGUGUUCAC CAUGGAACAU UUUGAUUAUA   2712

GUUAAUCCUU CUAUCUUGAA UCUUCUAGAG AGUUGCUGAC CAACUGACGU AUGUUUCCCU   2772

UUGUGAAUUA AUAAACUGGU GUUCUGGUUC                                    2802

(2) INFORMATION FOR SEQ ID NO:2:

(i) SEQUENCE CHARACTERISTICS:
        (A) LENGTH: 461 amino acids
```

(B) TYPE: amino acid
        (D) TOPOLOGY: linear (ii) MOLECULE TYPE: protein (xi) SEQUENCE DESCRIPTION: SEQ ID NO:2:

Met Gln Arg Val Asn Met Ile Met Ala Glu Ser Pro Gly Leu Ile Thr
-46 -45             -40             -35

Ile Cys Leu Leu Gly Tyr Leu Leu Ser Ala Glu Cys Thr Val Phe Leu
-30             -25             -20                         -15

Asp His Glu Asn Ala Asn Lys Ile Leu Asn Arg Pro Lys Arg Tyr Asn
            -10             -5                          1

Ser Gly Lys Leu Glu Glu Phe Val Gln Gly Asn Leu Glu Arg Glu Cys
        5               10              15

Met Glu Glu Lys Cys Ser Phe Glu Glu Ala Arg Glu Val Phe Glu Asn
        20              25              30

Thr Glu Arg Thr Thr Glu Phe Trp Lys Gln Tyr Val Asp Gly Asp Gln
35              40              45                      50

Cys Glu Ser Asn Pro Cys Leu Asn Gly Gly Ser Cys Lys Asp Asp Ile
                55              60              65

Asn Ser Tyr Glu Cys Trp Cys Pro Phe Gly Phe Glu Gly Lys Asn Cys
            70              75              80

Glu Leu Asp Val Thr Cys Asn Ile Lys Asn Gly Arg Cys Glu Gln Phe
        85              90              95

Cys Lys Asn Ser Ala Asp Asn Lys Val Val Cys Ser Cys Thr Glu Gly
        100             105             110

Tyr Arg Leu Ala Glu Asn Gln Lys Ser Cys Glu Pro Ala Val Pro Phe
115             120             125                     130

Pro Cys Gly Arg Val Ser Val Ser Gln Thr Ser Lys Leu Thr Arg Ala
            135             140             145

Glu Ala Val Phe Pro Asp Val Asp Tyr Val Asn Ser Thr Glu Ala Glu
            150             155             160

Thr Ile Leu Asp Asn Ile Thr Gln Ser Thr Gln Ser Phe Asn Asp Phe
        165             170             175

Thr Arg Val Val Gly Gly Glu Asp Ala Lys Pro Gly Gln Phe Pro Trp
180             185             190

Gln Val Val Leu Asn Gly Lys Val Asp Ala Phe Cys Gly Gly Ser Ile
195             200             205                     210

Val Asn Glu Lys Trp Ile Val Thr Ala Ala His Cys Val Glu Thr Gly
            215             220             225

Val Lys Ile Thr Val Val Ala Gly Glu His Asn Ile Glu Glu Thr Glu
            230             235             240

His Thr Glu Gln Lys Arg Asn Val Arg Ile Ile Pro His His Asn
        245             250             255

Tyr Asn Ala Ala Ile Asn Lys Tyr Asn His Asp Ile Ala Leu Leu Glu
        260             265             270

Leu Asp Glu Pro Leu Val Leu Asn Ser Tyr Val Thr Pro Ile Cys Ile
275             280             285             290

Ala Asp Lys Glu Tyr Thr Asn Ile Phe Leu Lys Phe Gly Ser Gly Tyr
            295             300             305

Val Ser Gly Trp Gly Arg Val Phe His Lys Gly Arg Ser Ala Leu Val
            310             315             320

Leu Gln Tyr Leu Arg Val Pro Leu Val Asp Arg Ala Thr Cys Leu Arg
        325             330             335

```
Ser Thr Lys Phe Thr Ile Tyr Asn Asn Met Phe Cys Ala Gly Phe His
    340                 345                 350

Glu Gly Gly Arg Asp Ser Cys Gln Gly Asp Ser Gly Gly Pro His Val
355                 360                 365                 370

Thr Glu Val Glu Gly Thr Ser Phe Leu Thr Gly Ile Ile Ser Trp Gly
                375                 380                 385

Glu Glu Cys Ala Met Lys Gly Lys Tyr Gly Ile Tyr Thr Lys Val Ser
                390                 395                 400

Arg Tyr Val Asn Trp Ile Lys Glu Lys Thr Lys Leu Thr
            405                 410                 415
```

(2) INFORMATION FOR SEQ ID NO: 3:

(i) SEQUENCE CHARACTERISTICS:
        (A) LENGTH: 2340 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO: 3:

```
ACCACUUUCA CAACUUGCUA GCAGAGGUUA UGCAGCGCGU GAACAUGAUC AUGGCAGAAU      60
CACCAGGCCU CAUCACCAUC UGCCUUUUAG GAUAUCUACU CAGUGCUGAA UGUACAGUUU     120
UUCUUGAUCA UGAAAACGCC AACAAAAUUC UGAAUCGGCC AAAGAGGUAU AAUUCAGGUA     180
AAUUGGAAGA GUUUGUUCAA GGGAACCUUG AGAGAGAAUG UAUGGAAGAA AAGUGUAGUU     240
UUGAAGAAGC ACGAGAAGUU UUUGAAAACA CUGAAAGAAC AACUGAAUUU UGGAAGCAGU     300
AUGUUGAUGG AGAUCAGUGU GAGUCCAAUC CAUGUUUAAA UGGCGGCAGU UGCAAGGAUG     360
ACAUUAAUUC CUAUGAAUGU UGGUGUCCCU UUGGAUUUGA AGGAAAGAAC UGUGAAUUAG     420
AUGUAACAUG UAACAUUAAG AAUGGCAGAU GCGAGCAGUU UUGUAAAAAU AGUGCUGAUA     480
ACAAGGUGGU UUGCUCCUGU ACUGAGGGAU AUCGACUUGC AGAAAACCAG AAGUCCUGUG     540
AACCAGCAGU GCCAUUUCCA UGUGGAAGAG UUUCUGUUUC ACAAACUUCU AAGCUCACCC     600
GUGCUGAGGC UGUUUUUCCU GAUGUGGACU AUGUAAAUUC UACUGAAGCU GAAACCAUUU     660
UGGAUAACAU CACUCAAAGC ACCCAAUCAU UAAUGACUUC ACUCGGGUU GUUGGUGGAG       720
AAGAUGCCAA ACCAGGUCAA UUCCCUUGGC AGGUUGUUUU GAAUGGUAAA GUUGAUGCAU     780
UCUGUGGAGG CUCUAUCGUU AAUGAAAAAU GGAUUGUAAC UGCUGCCCAC UGUGUUGAAA     840
CUGGUGUUAA AAUUACAGUU GUCGCAGGUG AACAUAAUAU UGAGGAGACA GAACAUACAG     900
AGCAAAAGCG AAAUGUGAUU CGAAUUAUUC UCACCACAA CUACAAUGCA GCUAUUAAUA      960
AGUACAACCA UGACAUUGCC CUUCUGGAAC UGGACGAACC CUUAGUGCUA AACAGUUACG    1020
UUACACCUAU UUGCAUUGCU GACAAGGAAU ACACGAACAU CUUCCUCAAA UUUGGAUCUG    1080
GCUAUGGGAG AAUUUCAUAU UUUACCUGAG CAAAUUGAUU AGAAAAUGGA ACCACUAGAG    1140
GAAUAUAAUG UGUUAGGAAA UUACAGUCAU UUCUAAGGGC CCAGCCCUUG ACAAAAUUGU    1200
GAAGUUAAAU UCUCCACUCU GUCCAUCAGA UACUAUGGUU CUCCACUAUG GCAACUAACU    1260
CACUCAAUUU UCCCUCCUUA GCAGCAUUCC AUCUUCCCGA UCUUCUUUGC UUCUCCAACC    1320
AAAACAUCAA UGUUUAUUAG UUCUGUAUAC AGUACAGGAU CUUGGUCUA CUCUAUCACA     1380
AGGCCAGUAC CACACUCAUG AAGAAAGAAC ACAGGAGUAG CUGAGAGGCU AAAACUCAUC    1440
AAAAACACUA CUCCUUUUCC UCUACCCUAU UCCUCAAUCU UUUACCUUUU CCAAAUCCCA    1500
AUCCCCAAAU CAGUUUUUCU CUUUCUUACU CCCUCUCUCC CUUUUACCCU CCAUGGUCGU    1560
```

-continued

```
UAAAGGAGAG AUGGGGAGCA UCAUUCUGUU AUACUUCUGU ACACAGUUAU ACAUGUCUAU   1620

CAAACCCAGA CUUGCUUCCA UAGUGGGGAC UUGCUUUUCA GAACAUAGGG AUGAAGUAAG   1680
GUGCCUGAAA AGUUUGGGGG AAAAGUUUCU UUCAGAGAGU UAAGUUAUUU UAUAUAUAUA   1740

AUAUAUAUAU AAAAUAUAUA AUAUACAAUA UAAAUAUAUA GUGUGUGUGU GUAUGCGUGU   1800

GUGUAGACAC ACACGCAUAC ACACAUAUAA UGGAAGCAAU AAGCCAUUCU AAGAGCUUGU   1860

AUGGUUAUGG AGGUCUGACU AGGCAUGAUU UGACGAAGGC AACAUUGGCA UAUCAUUGUA   1920

ACUAAAAAAG CUGACAUUGA CCCAGACAUA UUGUACUCUU UCUAAAAAUA AUAAUAAUAA   1980

UGCUAACAGA AAGAAGAGAA CCGUUCGUUU GCAAUCUACA GCUAGUAGAG ACUUUGAGGA   2040

AGAAUUCAAC AGUGUGUCUU CAGCAGUGUU CAGAGCCAAG CAAGAAGUUG AAGUUGCCUA   2100

GACCAGAGGA CAUAAGUAUC AUGUCUCCUU UAACUAGCAU ACCCCGAAGU GGAGAAGGGU   2160

GCAGCAGGCU CAAAGGCAUA AGUCAUUCCA AUCAGCCAAC UAAGUUGUCC UUUUCUGGUU   2220

UCGUGUUCAC CAUGGAACAU UUUGAUUAUA GUUAAUCCUU CUAUCUUGAA UCUUCUAGAG   2280

AGUUGCUGAC CAACUGACGU AUGUUUCCCU UUGUGAAUUA AUAAACUGGU GUUCUGGUUC   2340
```

(2) INFORMATION FOR SEQ ID NO: 4:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 4:

```
CACCAAGCTT CATCACCATC TGCC                                          24
```

(2) INFORMATION FOR SEQ ID NO: 5:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 5:

```
GGGTGACTGC AGTCCTGGTC CC                                            22
```

(2) INFORMATION FOR SEQ ID NO: 6:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 6:

```
GAGGAGACAG AACATACAGA GC                                            22
```

(2) INFORMATION FOR SEQ ID NO: 7:

(i) SEQUENCE CHARACTERISTICS:
(A) LENGTH: 23 base pairs
(B) TYPE: nucleic acid
(C) STRANDEDNESS: single -continued (D) TOPOLOGY: linear (ii) MOLECULE TYPE: cDNA (xi) SEQUENCE DESCRIPTION: SEQ ID NO: 7:

CAGGTAAAAT ATGAAATTCT CCC                                           23

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

GCTTCTGGGG TCTACCAGGA AC                                            22

(2) INFORMATION FOR SEQ ID NO: 9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

TATAACCCGG GAAATCCATC TTTCATTAAG T                                  31

(2) INFORMATION FOR SEQ ID NO: 10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO: 10:

AUCUGGCUAU GUAAGUGG                                                 18

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO: 11:

UUUCUCUUUA CAGGGGAGAA                                               20

(2) INFORMATION FOR SEQ ID NO: 12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: mRNA -continued

```
    (xi) SEQUENCE DESCRIPTION: SEQ ID NO: 12:

AUCUGGCUAU                                                              10

(2) INFORMATION FOR SEQ ID NO: 13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO: 13:

YYYYYYNCAG                                                              10

(2) INFORMATION FOR SEQ ID NO: 14:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO: 14:

UUUCUCUUUA CAG                                                          13
```